United States Patent
Logan et al.

(10) Patent No.: US 8,206,323 B2
(45) Date of Patent: Jun. 26, 2012

(54) METHOD AND APPARATUS TO DETECT AMBULATION

(75) Inventors: Beth Logan, Cambridge, MA (US); Matthai Philipose, Seattle, WA (US)

(73) Assignee: Intel-GE Care Innovations LLC, Roseville, CA (US)

( * ) Notice: Subject to any disclaimer, the term of this patent is extended or adjusted under 35 U.S.C. 154(b) by 1221 days.

(21) Appl. No.: 11/963,278

(22) Filed: Dec. 21, 2007

(65) Prior Publication Data

US 2009/0163835 A1    Jun. 25, 2009

(51) Int. Cl.
*A61B 5/103*    (2006.01)
*A61B 5/117*    (2006.01)

(52) U.S. Cl. .................................... 600/595

(58) Field of Classification Search ........... 600/587–595
See application file for complete search history.

(56) References Cited

OTHER PUBLICATIONS

David H. Friedman, Pseudo-Maximum-Likelihood Speech Pitch Extraction, IEEE Transactions on Acoustics, Speech, and Signal Processing, vol. ASSP-25, No. 3, Jun. 1997, pp. 213-221.

*Primary Examiner* — Max Hindenburg
*Assistant Examiner* — Jonathan M Foreman
(74) *Attorney, Agent, or Firm* — Pillsbury Winthrop Shaw Pittman LLP

(57) ABSTRACT

Low frequency harmonics detected by an accelerometer in a wrist-mounted device are used to infer ambulation. The fundamental rhythm or pitch is extracted from gathered accelerometer data and the determined pitch and associated properties are used to infer whether a subject is walking or not walking.

5 Claims, 4 Drawing Sheets

METHOD AND APPARATUS TO DETECT AMBULATION

FIELD

This disclosure relates to monitoring everyday human activities and in particular to monitoring ambulation.

BACKGROUND

As the population ages, sensing devices are being developed to allow everyday human activities to be automatically inferred. These sensing devices can support long term care while maintaining the independence valued by elders. Information about the daily activities of elders may be gathered remotely and provided to caregivers. Information about missed activities or changes in activity patterns may indicate that the elder is feeling ill. The ability to monitor everyday activities may enable the elderly to continue living in their own homes as long as possible.

BRIEF DESCRIPTION OF THE DRAWINGS

Features of embodiments of the claimed subject matter will become apparent as the following detailed description proceeds, and upon reference to the drawings, in which like numerals depict like parts, and in which:

Although the following Detailed Description will proceed with reference being made to illustrative embodiments of the claimed subject matter, many alternatives, modifications, and variations thereof will be apparent to those skilled in the art. Accordingly, it is intended that the claimed subject matter be viewed broadly, and be defined only as set forth in the accompanying claims.

DETAILED DESCRIPTION

The monitoring of daily activities is especially important when a person is experiencing cognitive decline in order to provide feedback on their wellbeing. The feedback may be based on the detection of various activities such as ambulation, eating, and hygiene. Ambulation is typically monitored using a hip or leg-mounted accelerometer that may be included in a pedometer to detect movement of the legs.

Eating and hygiene may be monitored by monitoring movement of the hands because the hands interact with many more objects than any other part of the body. For example, a Radio Frequency Identification (RFID) reader included in a bracelet worn at the wrist (wrist-mounted sensor) may be used to read RFID tags which have been placed on key objects associated with different activities. An RFID tag may be placed on a refrigerator door to detect when a person opens the refrigerator door. The detection of the opening of the refrigerator door may be used to infer that the person is eating.

The RFID bracelet may also include a motion detector that detects motion. The detection of motion may be used to infer an activity that is being performed by the person. For example, if a rapid back and forth hand movement is detected by the accelerometer in conjunction with an RFID tagged object identified as a toothbrush, it may be inferred that the activity is teeth brushing.

An embodiment of the present invention monitors ambulation using a device worn at the wrist that is also used to detect other activities. An RFID bracelet worn (placed) at the wrist of the person's dominant hand includes an in-built accelerometer that may be used to monitor ambulation according to the principles of the present invention. The accelerometer senses the motion of the trajectory of motion of the person's wrist. This is preferable as only one device needs to be worn and maintained in order to monitor multiple activities. In addition, the method and apparatus for inferring ambulation is very robust to the speed of walking.

Figure 1:
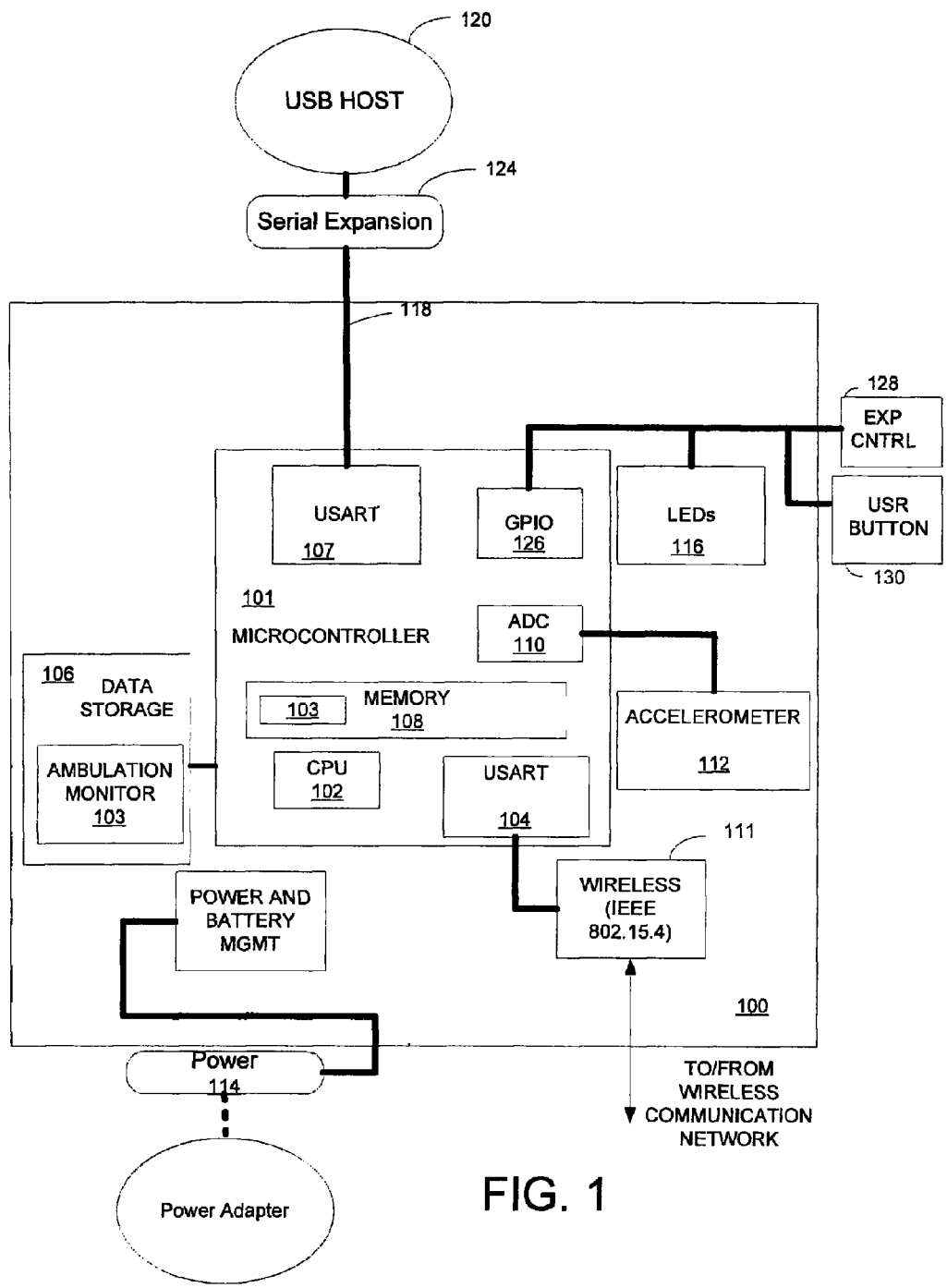
FIG. 1 is a block diagram of an embodiment of a sensing device that may be included in a Radio Frequency Identification (RFID) bracelet to allow ambulation to be monitored according to the principles of the present invention.

FIG. 1 is a block diagram of an embodiment of a sensing device 100 that may be included in an RFID bracelet to allow ambulation to be monitored according to the principles of the present invention. The sensing device 100 includes one or more action sensors for detecting events. In an embodiment, an action sensor may be an accelerometer sensor, switch or set of switches. In addition to action sensors in the sensing device, other action sensors may be connected to the sensing device 100 through a serial expansion port 124 or through an expansion port 128. In the embodiment shown in FIG. 1, a user button 130 is shown coupled to the sensing device 100.

The sensing device 100 includes a microcontroller 101 that controls the operation of the sensing device 100 and may communicate to various peripherals through internal and external expansion modules. In the embodiment shown in FIG. 1, the microcontroller 101 includes a General Purpose Input/Output Interface (GPIO) 126, an Analog-to-Digital converter (ADC) interface 110, two Universal Asynchronous/Synchronous Receive/Transmit serial communication (USART)s 104, 107, memory 108, and a Central Processing Unit (CPU) 102. The ADC interface 110 is used to capture sensor data from one or more Analog-to-Digital converter (ADC) channels. In an embodiment, there may be up to eight ADC channels. In an embodiment, the memory 108 may be Random Access Memory (RAM), or Flash memory (non-volatile memory). The Flash memory may store both data and instructions (code). The code stored in the Flash memory may include functions for collecting events detected by the sensing device 100 and transmitting these events to a collection device over a communications network.

The microcontroller 101 may also include a Central Processing Unit (CPU) 102 that may be a 16-Bit Reduced Instruction Set Computer (RISC) CPU. In order to maintain low-power usage, the ADC interface 110 may be disabled when not in use and re-enabled when necessary. The USARTs 104, 107 enable serial peripheral interface (SPI) and asynchronous UART functionality. In an embodiment, one of the USARTs 104, 107 allows Inter-Integrated Circuit (I2C) communication and has two specific Direct Memory Access (DMA) channels to ensure maximum throughput with data rates up to 400 Kbps. In an embodiment, the Institute of Electrical and Electronics Engineers (IEEE) 802.15.4 wireless network communications interface 111 is connected to the USART 104 using Serial Peripheral Interface (SPI) mode. The GPIO interface 126 provides an interface to I/O devices such as Light-emitting diodes (LEDs) 116. The LEDs 116 may be used as status indicators to indicate the current state of the sensing device 100.

An optional memory device, for example, data storage 106 may be coupled to the microcontroller 101. In one embodiment the optional memory device is a flash memory device that may store up to 2 Giga bits of data. The optional memory device allows the additional storage of data while the sensing device 100 is not streaming data to a host device over the wired and/or wireless communication networks. The data storage 106 may be used to store accelerometer data allowing for continuous operation and also providing a dual copy of data allowing sensed data to be transmitted over the communication network.

In an embodiment the ADC interface 110 may support up to eight ADC channels for 12-bit Analog/Digital (A/D) conversions using a 16 word conversion-and-control buffer which enables data to be read and stored without the need for CPU intervention. External ADC ports may be utilised for reading data from an accelerometer 112

The accelerometer 112 may be coupled to the ADC interface 110 to enable reading of 3-dimensional acceleration. In an embodiment, the accelerometer 112 may be a Freescale Semiconductor™ 3-axis (XYZ) accelerometer. The accelerometer 112 may be connected to the microcontroller 101 via three channels of ADC. An internal expansion through the ADC interface 110 allows modules that support other sensing functions to be coupled to the sensing device 100.

In an embodiment, a signal captured by a sensor device coupled to the sensing device 100 received at an ADC port may be forwarded by the microcontroller 101 to a processing (collection) device over a wireless communication network through the wireless module 111. In another embodiment, the signal may be processed by an ambulation monitor 103 stored in memory 108 or in data storage 106.

In an embodiment support for wireless network communication is provided by an IEEE 802.15.4 radio module. The IEEE 802.15.4 radio module may be connected to the CPU directly via the USART 104. In another embodiment support for wireless network communications may be provided by a Bluetooth® module.

Figure 2A:
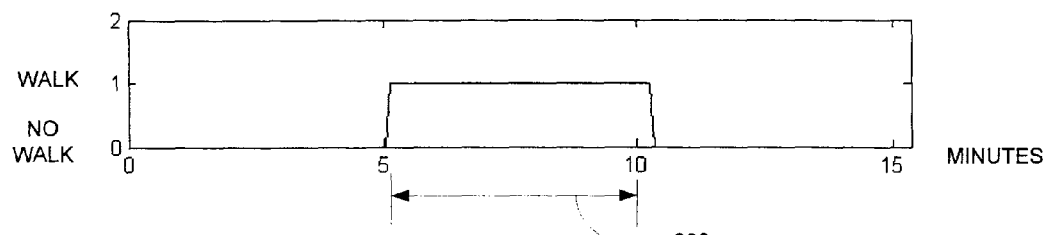
FIGS. 2A-2E are plots that illustrate data collected from a wrist-mounted accelerometer in an embodiment of the sensing device shown in FIG. 1.

FIGS. 2A-2E are plots that illustrate data collected from a wrist-mounted accelerometer in an embodiment of the sensing device 100 shown in FIG. 1. The accelerometer may be a 3 axis accelerometer 112 as shown in FIG. 1. The 3-axis accelerometer has three axes that may be referred to as the x, y and z axis. Each plot has two axes, referred to as the X-axis and the Y-axis. The X-axis of the plot shown in FIG. 2A is time (T) in minutes from 0 to 15 and the Y-axis of the plot indicates the time period during which the subject walked 200, with the value 0 indicating that the subject was not walking and the value 1 indicating that the subject was walking. In the example shown, the subject walked for just over five of the fifteen minutes from the five minute mark (5) to just after the ten minute mark (10) shown as walking time period 200 on the X-axis of the plot.

Figure 2B:
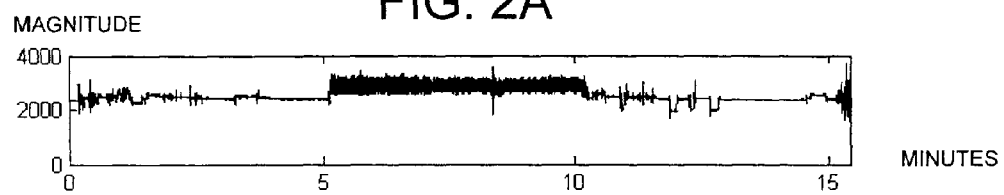

FIG. 2B is a plot of data collected by one of the three axes (x, y, z) of the 3-axis accelerometer 112. In the example shown, the data was collected on the x-axis of the accelerometer. Similar plots may be collected from the other two axes (y, z) of the 3-axis accelerometer. The X-axis of the plot shows time (T) in minutes from 0 to 15 minutes. The Y-axis of the plot shows the signal output on the x-axis of the accelerometer. The value of the output signal on the Y-axis of the plot is related to the number of g's of acceleration of the x-axis of the 3-axis accelerometer where:

number of g's of acceleration=2.5*y/(4095*0.3)−1.5/0.3

Referring to the plot shown in FIG. 2B, from time 5 to 10, while the subject is walking, the number of g's of acceleration is higher than when the subject is not walking. However, the number of g's of acceleration may also increase due to excessive wrist movement while the subject is not walking. For example, excessive wrist movement may also be observed while the subject is talking. The increase in the number of g's of acceleration due to excessive wrist motion alone can be observed in the plot shown in FIG. 2B around time 15 when there is a high energy signal due to the subject taking off the wrist-mounted accelerometer.

Figure 2C:
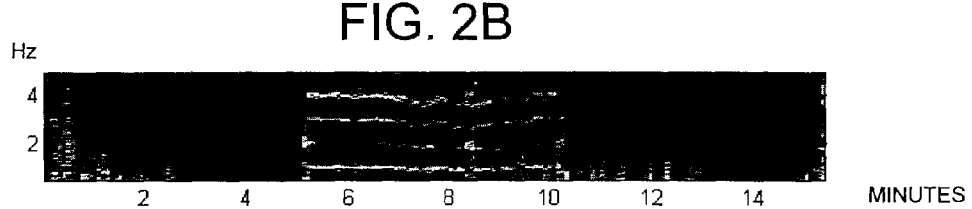

FIG. 2C is a plot of a spectrum of data derived from combining the magnitude of the signal at the x, y and z axis of the 3-axis accelerometer 112. By combining the magnitude from all of the axis of the 3-axis accelerometer 112, the spectrum in FIG. 2C is independent of the accelerometer orientation. The Y-axis of the plot is the frequency of the spectrum measured in Hertz (Hz) and the X-axis of the plot is time. During the time period from 5 to 10 in which the subject is walking, frequency bands or "harmonics" can be observed, in this case spaced at slightly less than 1 Hz. This is a somewhat surprising result showing that there is regular movement in the wrist while walking, that is, there is regular movement of the wrist while the legs are moving, indicating that the fundamental movement of the subject when walking generates low frequency harmonics that may be detected in the wrist. Thus, the low frequency harmonics that are observed at the wrist may be used to infer ambulation.

An estimate of the pitch (a property that is dependent on frequency of waves) associated with the low frequency harmonics due to regular movement of the wrist may be computed. The estimated pitch may be used to determine whether the low frequency harmonics infer ambulation.

Figure 2D:
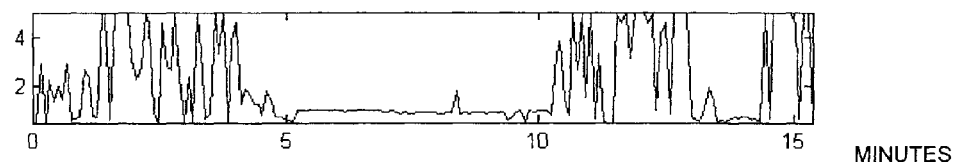
Figure 2E:
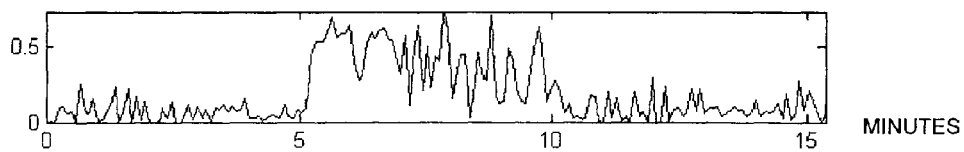

FIGS. 2D and 2E illustrate how the low frequency harmonics observed in the wrist may be used to infer whether a subject is walking or not walking. FIG. 2D is a plot of time (X-axis) versus a pitch estimate extracted from the signal shown in FIG. 2B (Y-axis). FIG. 2E is a plot of time (X-axis) versus a measure of the maximum "goodness" of a pitch estimate of the signal shown in FIG. 2B (also referred to as maxR1) (Y-axis).

Referring to FIG. 2D, the pitch estimate has a low variance in the period from 5 minutes to 10 minutes, that is when the subject is walking. We have found this to be true regardless of the actual value of the pitch that is, the speed at which the subject is walking. Thus, the pitch variance is robust to variations, for example, in the speed and style of walking.

Referring to FIG. 2E, the measure of the maximum "goodness" of the pitch estimate is high, that is, over 0.5 in the region between 5 and 10 minutes on the X-axis of the plot. Thus, the estimated pitch in the region of the X-axis of the plot between 5 minutes and 10 minutes is a good indicator that the subject is walking. The goodness of the pitch estimate at about 15 on the X-axis of the plot is not as high and thus it may be inferred that the subject is not walking, that is, that the movement of the wrist during this time period is not due to walking.

Thus, when the maximum goodness of a pitch estimate of the signal is high, for example, close to about 0.5, the signal has a fundamental "pitch" and therefore it may be inferred with confidence that the subject is walking.

Features derived from the extracted pitch estimation and maximum goodness of the pitch estimation are compared with a model that may be generated by decision tree classifiers. The decision tree classifiers are built to learn whether a subject is walking versus non-walking and trained on data using features derived from maximum goodness of the pitch estimation and the pitch estimation. In an embodiment, the features derived from maximum goodness of the pitch estimation and pitch estimation are (1) maximum goodness of the pitch estimation smoothed over windows and (2) the variance of the pitch.

Figure 3:
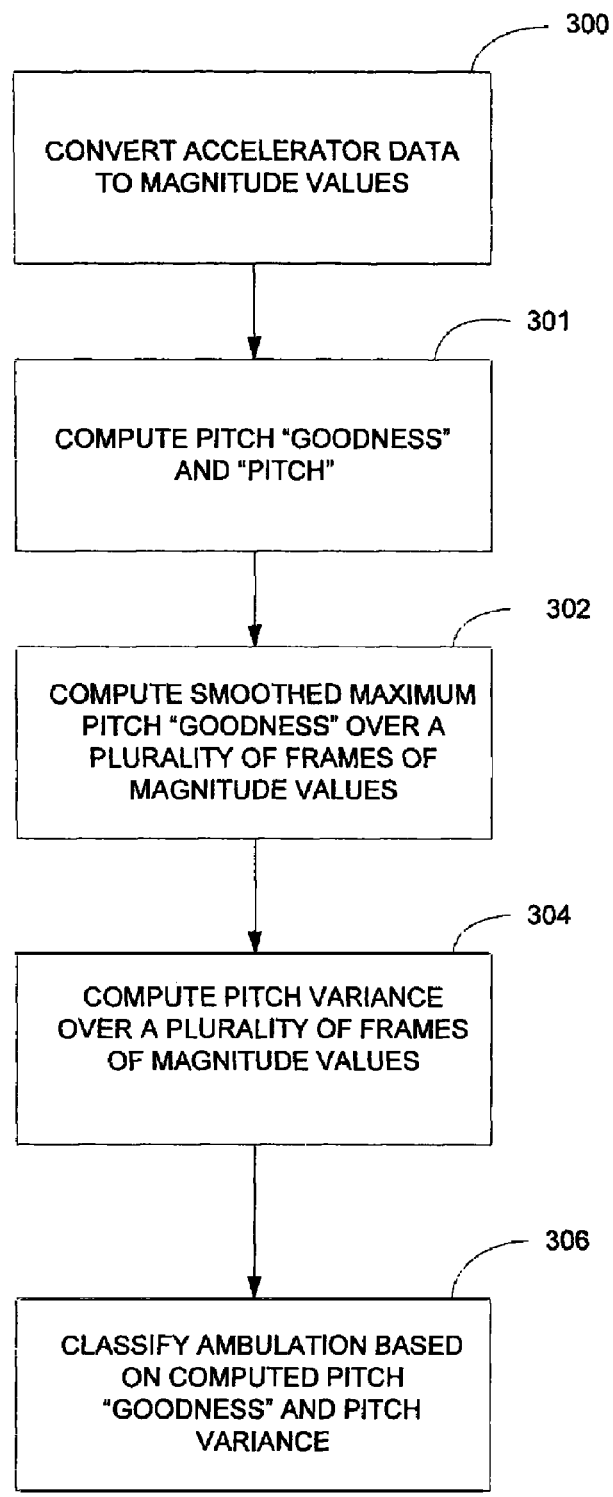
FIG. 3 is a flowgraph illustrating an embodiment of a method used to infer ambulation that may be performed by the ambulation monitor in the sensing device shown in FIG. 1.

FIG. 3 is a flowgraph illustrating an embodiment of a method used to infer ambulation that may be performed by the ambulation monitor 103 in the sensing device 100 shown in FIG. 1.

At block 300, the received raw data signal from each axis of the accelerometer 112 (for example, the x-axis of the 3-axis accelerometer shown in the plot in FIG. 2B) is sampled at a selected low sample rate. The sample rate is dependent on the highest frequency and pitch related to detection of ambulation. A typical walking speed is in the range of 0 Hz to 5 Hz and a typical sampling rate is 50 Hz. In an embodiment in which the accelerometer 112 has three axes (x, y, z), the raw data signal from each of the axes is sampled. In an embodiment, a frame of samples taken over a five second time period on any one of the three axes (x, y, z) may include about 250 samples. Each frame of data is assumed to have a constant pitch for the duration of the frame. The pitch may vary from frame to frame as the subject walks at different speeds or stops walking altogether. The three frames of samples (from the three axes (x, y, z)) are converted to a single frame of magnitude values. An embodiment of a method for performing the conversion from three axes (x, y, z) to a single frame of magnitude values will be described later in conjunction with FIG. 4. Processing continues with block 301.

At block 301, a function is performed on each frame of magnitude values to determine maximum "goodness" of the pitch and the pitch. As discussed earlier, pitch is a measured fundamental frequency of a signal. In an embodiment, an algorithm that computes pitch and pitch "goodness" from a speech signal may be applied to an analog signal received from any axis of a 3-axis accelerometer. For example, "Pseudo-Maximum-Likelihood Speech Pitch Extraction", D. Friedman, IEEE Transactions on Acoustics, Speech and Signal Processing, Vol ASSP-25, No 3, June 1977 discusses an algorithm that computes the pitch and "maxR1", a measure of the maximum "goodness" (measure of confidence) of the pitch estimate from a speech signal.

The algorithm presented by Friedman assumes that signal s is an observation of a true periodic signal $s_0$ with pitch period to, i.e. $s_0(t)=s_0(t+kt_0)$, k=0, 1, 2, . . . . The algorithm finds $t_0$ such that:

$$\text{Integral over all } t[(s(t)-s_0(t))^2 . w(t)] \quad (1)$$

is a minimum, where w(t) is a windowing function used to look at only one frame of the signal. A typical windowing function is a Hamming window w(n) which is computed as follows:

$$w(t)=0.53836-0.46164 \cos(2*pi*t/N-1)$$

where N is the frame size.

The solution to equation (1) above is a function with peaks at likely pitch periods. The higher the peak the better the pitch candidate. The maximum of this function may be used as a measure of the "goodness" of the pitch and the inverse of the period as the pitch. Processing continues with block 302.

At block 302, the average maximum pitch "goodness" (average goodness of pitch estimate) is computed over a plurality of frames. In an embodiment, the number of frames is three to five. Processing continues with block 304.

At block 304, pitch variance is computed given the pitch computed in block 301. In an embodiment, pitch variance may be computed using pitch values from five frames. Processing continues with block 306.

At block 306, a decision tree classifier compares the computed average maximum pitch "goodness" and the pitch variance with learned values to determine if the subject is walking or not walking. For example, if the average maximum pitch "goodness" is less than a minimum value, the subject is not walking irrespective of the pitch value. If the average maximum pitch "goodness" is greater than a minimum value, then the value of the pitch variance is additionally used to determine if the subject is walking.

The output of the classifier is a decision indicating whether the subject is walking or not walking. For example, referring to the plots shown in FIGS. 2D and 2E, during the time period between 5 and 10 minutes the value of the maximum of the goodness of the pitch and the pitch variance may be classified as "walking". In an embodiment, the classifier may classify a value of maximum goodness of pitch greater than 0.5 and a pitch variance of 0.2 as walking and a value of maximum good of pitch of 0.1 and a pitch variance of 10 as not walking.

Figure 4:
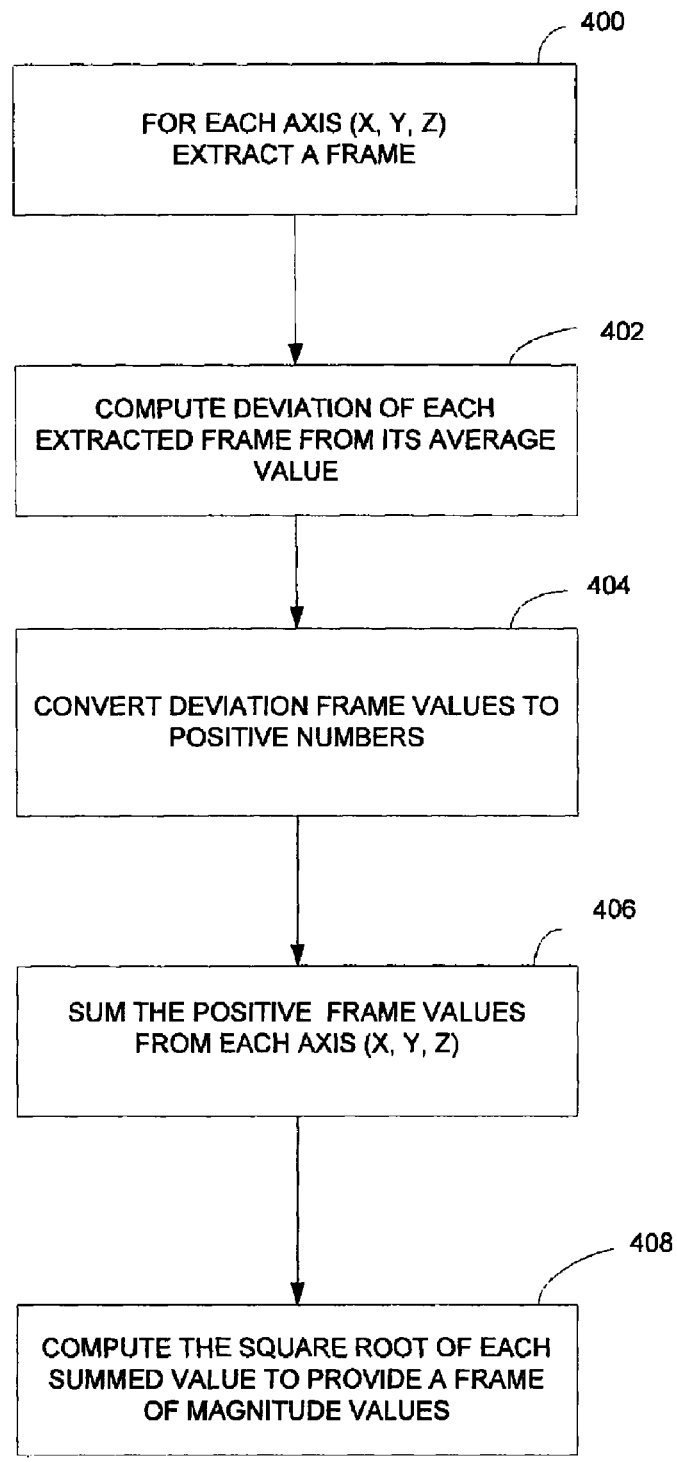
FIG. 4 is a flowgraph illustrating an embodiment of a method used to convert axis data received from an accelerometer to magnitude values.

FIG. 4 is a flowgraph illustrating an embodiment of a method used to convert axis data received from an accelerometer to magnitude values.

At block 400, a frame of samples is extracted from each axis of the 3-axis accelerometer (for example, axis x, y and z). The number of samples in the frame is dependent on the sample rate as discussed earlier. Processing continues with block 402.

At block 402, the mean of the sample points is computed and the mean is subtracted from each sample point to allow the deviation from the average value to be determined. For example, if there are three sample points {2001, 2002, 2004}, the mean is 2002, that is, the result of (2001+2002+2004)/3. The values after subtracting the mean from each of the three sample points are {−1, 0, 1}. Processing continues with block 404.

At block 404, as some of the values resulting from the subtraction of the mean are negative, the values are squared to make all values positive. For example, the result of squaring the values {−1, 0, 1} is {1, 0, 1}.

At block 406, the positive sample points from each frame of each axis are summed. For example, if the values from each of the axis are {1,1, 0}, {1.7, 7.1, 1.7} and {5675.1, 608.4, 2567.1}, the summed values from each of the axis are {5677.8, 610.4, 2568.8}. Processing continues with block 408.

At block 408, the square root of the sum of the magnitude of the acceleration is computed to provide a frame of magnitude values to represent the acceleration measured on all three axis of the accelerometer. For example, the square root of the values {5677.8, 610.4, 2568.8} is {75.4, 24.7, 50.7}. The computation of a single frame of magnitude values representing the acceleration on all three axes, reduces the sensitivity of the orientation of the accelerometer worn on the wrist. The single frame of magnitude values is independent of the placement of the accelerometer in the sensor placed on the wrist. In other embodiments, the 3 axis accelerometer may be replaced by a 2 axis accelerometer It will be apparent to those of ordinary skill in the art that methods involved in embodiments of the present invention may be embodied in a computer program product that includes a computer usable medium. For example, such a computer usable medium may consist of a read only memory device, such as a Compact Disk Read Only Memory (CD ROM) disk or conventional ROM devices, or a computer diskette, having a computer readable program code stored thereon.

While embodiments of the invention have been particularly shown and described with references to embodiments thereof, it will be understood by those skilled in the art that various changes in form and details may be made therein without departing from the scope of embodiments of the invention encompassed by the appended claims.

The invention claimed is:

1. An apparatus comprising:
an accelerometer in close proximity to a wrist; and
an ambulation detector to receive a signal having low-frequency harmonics from the accelerometer and to extract a measure of pitch variance and goodness of a pitch estimate of the received signal in order to infer ambulation.

2. The apparatus of claim 1, wherein the ambulation detector is configured to sample the signal to provide a plurality of frames of sample magnitude values.

3. The apparatus of claim 2, wherein the ambulation detector is configured to extract the measure of pitch variance and average goodness of pitch estimate from the plurality of frames of sample magnitude values.

4. The apparatus of claim 1, wherein the ambulation detector is configured to infer ambulation based on comparing the extracted measure of pitch variance and average goodness of pitch estimate with learned values of pitch variance and goodness of pitch estimate stored in a decision tree classifier.

5. The apparatus of claim 1, wherein the accelerometer has three axis and the ambulation detector is configured to receive a plurality of signals having low-frequency harmonics, each of the plurality of signals received from a different axis, and the ambulation detector to compute a magnitude signal by combining the three axis from which to extract the measure of pitch variance and average goodness of pitch estimate.

* * * * *